United States Patent [19]

Gerow

[11] Patent Number: 4,795,463

[45] Date of Patent: Jan. 3, 1989

[54] LABELED BREAST PROSTHESIS AND METHODS FOR DETECTING AND PREDICTING RUPTURE OF THE PROSTHESIS

[75] Inventor: Frank J. Gerow, Houston, Tex.

[73] Assignee: Baylor College of Medicine, Houston, Tex.

[21] Appl. No.: 41,886

[22] Filed: Apr. 23, 1987

Related U.S. Application Data

[63] Continuation-in-part of Ser. No. 657,301, Oct. 3, 1984.

[51] Int. Cl.⁴ ................................................ A61F 2/12
[52] U.S. Cl. ....................................................... 623/8
[58] Field of Search ...................... 623/1, 10, 11, 7, 8; 128/1 R, DIG. 21, 654, 774

[56] References Cited

U.S. PATENT DOCUMENTS 4,172,449 10/1979 LeRoy et al. ............................ 623/8

Primary Examiner—V. Millin
Assistant Examiner—David J. Isabella
Attorney, Agent, or Firm—Fulbright & Jaworski

[57] ABSTRACT

Disclosed is a prosthesis for implantation into human soft tissue which is constructed of a suitable implantable envelope and contents to form a breast shape when implanted, such as silicone gel, saline, or a combination of silicone gel and saline contained within a silicone elastomer envelope, which has been labeled with radioopaque markers. The envelope is labeled with a marker that absorbs electromagnetic energy to an extent different from that of the envelope, its contents and the human soft tissue in the breast cavity into which the prosthesis is implanted which makes possible the use of roentgenographic imaging to determine whether the envelope has ruptured or whether the envelope is folded persistently in a particular location increasing the probability that the envelope may rupture along the fold line. Also disclosed is a method for using roentgenography to determine whether the contents, such as silicone gel, have escaped from the envelope of the prosthesis by labeling the envelope with radioopaque materials, as mentioned above, and a method for determining whether fold-fault failure of the envelope of the implanted prostheses is likely to occur.

19 Claims, 2 Drawing Sheets

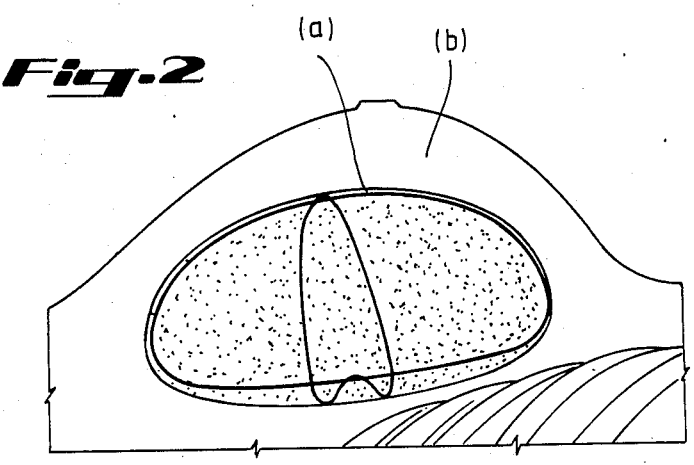
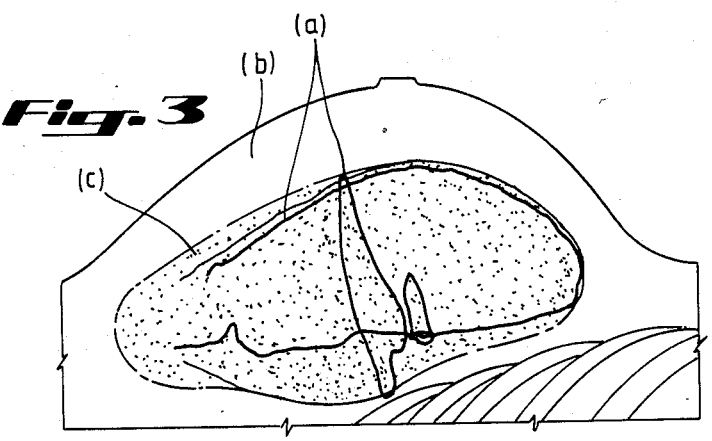
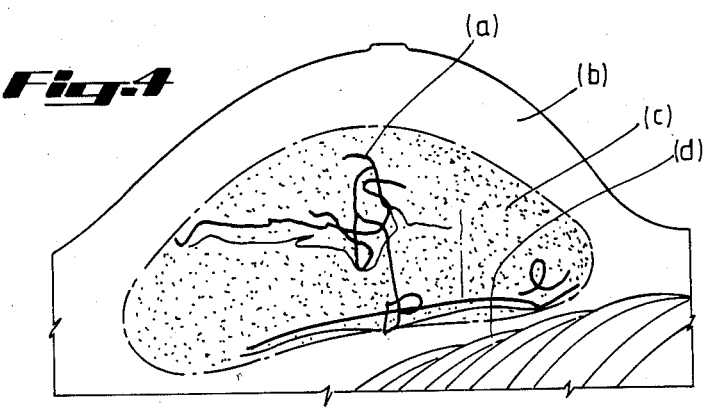

LABELED BREAST PROSTHESIS AND METHODS FOR DETECTING AND PREDICTING RUPTURE OF THE PROSTHESIS

CROSS-REFERENCE TO RELATED APPLICATIONS

The present application is a continuation-in-part of U.S. application Ser. No. 657,301, filed Oct. 3, 1984.

BACKGROUND OF THE INVENTION

Surgical procedures to alter the appearance of the human female breast comprise a substantial portion of the surgery performed by plastic surgeons. It has been estimated that 16 percent of the income derived by plastic surgeons in the United States results from such surgery. The surgical procedures frequently involve implantation of silicone based prostheses. Silicone implant mammoplasty is indicated in a variety of conditions, including cosmetic augmentation in micromastia, reconstructive augmentation in mammary asymmetry, and total reconstruction after mastectomy. The most commonly used breast implants are constructed of silicone gel contained within a silicone elastomer envelope. Less commonly used implants are constructed of a silicone elastomer envelope to which saline can be added to give the desired size or of a medical grade silicone gel-filled implant within a larger silicone elastomer envelope to which saline can be added. The first such implant of each type was developed approximately 20 years ago by the present applicant working in conjunction with another physician and with persons at Dow Corning Corporation. In the years since development, approximately one million pairs of these prostheses have been implanted; and, currently, they are being implanted at a rate of approximately one hundred thousand pairs per year.

Prior to development of the silicone elastomer enveloped, silicone gel prostheses, various agents were instilled directly into breasts to alter their appearance. Among the agents used were paraffin, processed petroleum, and silicone fluid. Usage of these directly instilled agents now is disfavored and largely has been discontinued because their use frequently was associated with local, often intense, inflammatory reactions. Additionally, migration of these instilled agents, particularly silicone fluid, has been associated with more generalized, potentially fatal tissue responses which vary depending upon into which tissue or structure the agent migrated. Human Adjuvant Disease may be a systemic effect of paraffin or silicone fluid instillation and is apparently an autoimmune connective tissue disorder that manifests as mixed connective tissue disease, rheumatoid arthritis, systemic scleroderma, or systemic lupus erythematosus. Onset of Adjuvant Disease has been reported as early as 2 years and as many as 25 years following instillation of breast augmentation agents such as paraffin or silicone fluid. In some cases, remission of the disease has followed removal of the augmentation agents; and in two cases, the disease has proved fatal.

Until recently, Adjuvant Disease had not been associated with implantation of silicone elastomer enveloped, silicone gel prostheses. However, within the last two years, there have been several reported cases where Adjuvant Disease followed implantation of these prostheses. In the only reported patient who developed Adjuvant Disease following prosthetic implantation where the prosthesis had been removed and examined, the silicone elastomer envelope was found to be ruptured; and free silicon gel was found free in the human cavity for the implant. Baldwin, C. M., and Kaplan, E. N., *Silicone-Induced Human Adjuvant Disease,* 10 Annals of Plastic Surgery 270 (1983). It also is known now that the silicone gel contained in these prostheses is composed of 96 to 98 percent extractable polydimethylsiloxanes (silicone fluid). Thus, the finding of Adjuvant Disease in a patient carrying a ruptured prosthesis combined with data establishing possible association of this disease with instillation of free silicone fluid indicates that the risk of developing Adjuvant Disease may be enhanced by rupture of silicone elastomer enveloped, silicone gel implants. Evidence suggests that patients predisposed to developing Adjuvant Disease are more susceptible to the disease following exposure to a foreign antigen.

Additionally, escape of the silicone gel from the envelope of the prosthesis is associated with other adverse consequences including satelliting of the gel into various parts of the soft tissue around the prosthetic pocket or down into the arm. Silicone gel in the soft tissue forms dense capsules and causes pain necessitating surgical excision of the gel. Recent data also suggest that the risk of infection in the tissue surrounding the prosthesis is increased following its rupture; and free silicone gel in the prosthetic pocket together with an infection may enhance synergistically the host tissue reactions to the implant. Therefore, ruptured prostheses should be removed as soon as possible; and if there is any evidence of infection or movement of the silicone gel away from the prosthetic cavity, ruptured prostheses should be removed immediately.

There are a number of causes of rupture of silicone elastomer enveloped, silicone gel prostheses. The prostheses can be punctured or torn accidentally during implantation procedures. If, after implantation, fluid which must be removed accumulates in the prosthetic pocket, a needle inserted to aspirate the fluid may pierce the silicone elastomer envelope. In 10 to 30 percent of patients receiving a prosthetic implant, a tight periprosthetic capsule forms which must be released. A closed capsulotomy, during which the breast is compressed forcefully by the surgeon's hands, is a procedure used to break the capsule and soften the feel of the breast. In approximately 30 percent of patients, a closed capsulotomy causes rupture of the prosthetic silicone elastomer envelope. Additionally, rupture of the silicone elastomer envelope can result from biodegradation of the envelope by tissue enzymes. Because of the relatively poor tear resistance of the silicone elastomer envelope, once a rupture or tear has occurred, it will propagate upon only minimal manipulation of the breast, freeing the silicone gel to escape into the prosthetic cavity and beyond.

Fold-fault failure also has been shown to be a cause of rupture of silicone elastomer envelopes, especially in prostheses containing saline. After implantation into the prosthetic cavity, the prosthetic envelope can become folded persistently along a particular line. By abrasion against itself along the fold line, the envelope progressively will wear away causing it to rupture along the fold line. Fold-fault failure of saline containing prostheses creates an emergency because the saline which leaks from the ruptured envelope is absorbed into the surrounding tissues. Absorption of the saline causes the prosthetic cavity to shrink. Thus, to avoid the need for a complete reoperation, rather than mere replacement of the prosthesis, the ruptured prosthesis must be removed immediately after rupture and replaced.

Although silicone elastomer enveloped silicone gel breast prostheses have been used extensively for 20 years and despite a demonstrated need to determine if silicone gel has escaped its envelop,, no prosthesis or non-invasive method has been developed which enables determination of whether implanted prostheses have ruptured prior to the onset of complication-related signs and symptoms. Also, no method has been developed to predict an impending fold-fault failure. In most cases, surgeons are unable to determine by external physical examination whether a prosthesis remains intact. Roentgenographic examination also has proved incapable of discerning the status of prosthetic envelopes because the X-ray density of the prosthetic envelope and its contents are not sufficiently different from the surrounding soft tissue to indicate whether there has been a rupture of the envelope or an impending fold-fault failure, and thus an escape or an impending escape of the contents into the cavity thus freeing the contents to migrate into surrounding or distant soft tissues.

This long-felt need for a prosthesis and a procedure which enables determination of whether implanted silicone elastomer enveloped, silicone gel implants remain intact now has been satisfied. Implantation of a prosthesis composed of a silicone elastomer envelope marked on the exterior of the envelope with a material, such as a radioopaque material, which absorbs electromagnetic energy to an extent different from the envelope, its contents, and the tissue surrounding it and enables production of an image of the marked envelope by irradiating the tissue bearing the marked implant with electromagnetic energy. An image showing that the pattern or configuration of the radioactive or radioopaque marker indicates that the envelope is intact. An image showing a change in the pattern or configuration of the radioopaque marker indicates that the envelope has ruptured or has a fold-fault which could develop into a rupture.

The material that absorbs electromagnetic energy to an extent different from the silicone elastomer envelope, the prosthesis contents, and the human soft tissue used to mark the silicone elastomer envelope can be incorporated within the envelope during manufacture or can be applied to the envelope following manufacture of the prosthesis. Marking the silicone elastomer envelope with one of several readily available radioopaque materials and producing an image by X-irradiation of the breast, as is done in mammography, has proved a successful application of this invention. The present innovation also is applicable to determining the status of other types of silicone elastomer enveloped, silicone gel prostheses and other types of silicone elastomer prostheses. Such other types of prostheses include various facial implants, penile implants, testicular implants, and carpal, metacarpal, and interphalangeal joint replacements and similar joint replacements used in the feet.

Further, marking the silicone elastomer envelope of saline containing prostheses provides a method for predicting fold-fault failure. To predict an impending failure, two or more serial electromagnetic energy produced images, such as mammograms, are compared. If the same fold line persists, the probability that rupture along that fold line will occur is enhanced. Also, a mammogram obtained while the breast was compressed along its lateral and medial aspects can be compared to one obtained absent breast compression. If a change in the initial pattern or configuration of the marker appears in the compressed and noncompressed mammograms, the probability of a rupture or that the identified fold line is persistent and will be a point of rupture is increased. Once a persistent fold line is detected, the surgeon can employ external manipulation or other techniques to alleviate the persistent fold, thus preventing rupture of the prosthetic envelope, or if necessary, remove the prosthesis and implant another one.

PRIOR ART STATEMENT

Applicant is unaware of any prior art teaching marking the silicone elastomer envelope of silicone gel containing prostheses with materials that absorb electromagnetic energy to an extent different from the prosthesis envelope, the prosthesis contents, and the human soft tissue, any prior art which teaches using electromagnetic energy to produce images of breast bearing implants so marked to ascertain whether the silicone elastomer envelopes of the prostheses have ruptured or any prior art which teaches using electromagnetic energy to produce images of breasts so marked to enable prediction of fold-fault failure of prosthetic silicone elastomer envelopes.

Prior art does teach the use of radioopaque markers to enable roentgenographic determination of the location of various types of medical devices. For example, catheters placed in the subclavian veins for administration of intravenous hyperalimentation bear X-ray detectable markers so that proper positioning of the catheter can be confirmed prior to initiation of administration of the hyperalimentation fluid. Similar position-indicating markers also are used on chest tubes, cardiac catheters, surgical sponges, and other intravascular devices. These markers enable roentgenographic determination of the course and location of the device; but no information about the volume or configuration of the device and no information about whether the device remains volumetrically intact can be gained using position-indicating markers.

The prior art also discloses a sensor, U.S. Pat. No. 4,172,449 (LeRoy, et. al.), implantable in the body to monitor body fluid pressure by radioopaque means inside the sensing body. LeRoy, et. al. addresses only an intact implant measuring internal pressures within its own system. LeRoy, et. al. must have an intact system and will fail if the system ruptures and will not indicate the rupture. LeRoy, et. al. does not speak to identify a broken implant and the configurations specified by LeRoy, et. al. would not identify the broken implant even if it occurred to the measuring device of LeRoy itself. LeRoy, et. al. requires a tube or connection delivering content from one container site to another to measure the pressure and requires another intact container site be present on the end of and connected to the tube or connector for this device to work.

Dow Corning Wright has made available for many years a silastic percutaneous skin expander; however, Dow Corning does not address in any way or provide any means or method for the identification of a broken implant or an implant with imminent fold-fault failure. While the Down Corning Wright expander has been available for a long period of time and there has been a long felt need for a prosthesis and a procedure which enables determination of whether an implanted expander remains intact or has an impending fold-fault failure, it is only the present invention which solves this problem and satisfies this need.

The prior art also teaches using radioopaque agents such as barium sulfate to determine the configuration and patency of the lumen of the gastrointestinal tract. Although the silicone gel contained within the envelope of a silicone-based prosthesis could be marked with barium sulfate, such marking would fail to provide any way of determining whether the marked gel was within or without the silicone elastomer envelope.

SUMMARY OF THE INVENTION

The present invention is directed to breast prostheses composed of a flexible envelope, such as a silicone elastomer envelope labeled with a radioopaque marker which absorbs electromagnetic energy different from the envelope and its contents and the soft tissue which surrounds the implanted prothesis in a manner, such as a pattern or configuration, which enables roentgenographic determination of whether the envelope has ruptured or has a fold-fault, to a method for using roentgenographic imaging to determine whether the envelopes have ruptured and to a method for using roentgenographic imaging to predict impending fold-fault failure of flexible envelopes, such as prosthetic silicone elastomer envelopes.

Accordingly, it is an object of the present invention to provide a breast prosthesis composed of a flexible envelope, such as a silicone elastomer envelope, and suitable contents which has been labeled with a radioopaque marker which absorbs electromagnetic energy different from the envelope and its contents and different from surrounding breast tissue and in a pattern or configuration which enables roentgenographic determination of whether the envelope is intact, has ruptured, or has an impending fold-fault rupture.

A further object of the present invention is to provide a method for using roentgenographic imaging to determine whether the flexible envelope, such as a silicone elastomer envelope, of a breast prosthesis is intact, has ruptured, or has an impending fold-fault rupture.

Other and further objects, features, and advantages appear throughout.

BRIEF DESCRIPTION OF THE DRAWINGS

FIG. 2 is a mammogram of a breast bearing a prosthesis marked in the pattern or configuration as in FIG. 1 wherein the silicone elastomer envelope of the prosthesis is intact.

FIG. 3 is a mammogram of a breast bearing a Prosthesis marked in the pattern or configuration as in FIG. 1 wherein the silicone elastomer envelope of the prosthesis has ruptured, and some of the silicone gel has escaped from the silicone elastomer envelope.

FIG. 4 is a mammogram of a breast bearing a prosthesis marked in the pattern or configuration as in FIG. 1 wherein the silicone elastomer envelope of the prosthesis has ruptured, and most of the silicone gel has escaped from the silicone elastomer envelope.

DESCRIPTION OF THE PREFERRED EMBODIMENTS

Although the present applicant recognizes that it is commercially preferable to incorporate the radioopaque material pattern into the flexible envelope, such as a silicone elastomer envelope, of a prosthesis during its manufacture, in this and the subsequent examples the radioopaque material was applied to the envelopes of previously manufactured prostheses. It is necessary that the marker material absorbs electromagnetic energy to an extent different from the materials of the envelope and its contents and different from the soft tissue in the implant cavity. Thus, for purposes of disclosure, a mammary prosthesis constructed of silicone gel contained within a soft, seamless silicone elastomer envelope is labeled with radioopaque material. The prosthesis selected is marketed by Wright Dow Corning, Inc., under its registered "Silastic" trademark. The radioopaque material was taken from roentgenographically-detectable surgical sponges sold by Johnson & Johnson Products, Inc., under its registered "Ray-Tec" trademark. The radioopaque material was attached to the prosthesis by positioning it on the prosthetic envelope, completely covering it with a small amount of silicone rubber, and recuring the prosthesis by heating to affix the radioopaque label to the envelope permanently.

For purposes of disclosure, the following examples are directed to presently preferred embodiments, in which the flexible envelope is made of silicone elastomer, and the contents are silica gel, saline, or a combination of both. The flexible envelope can be made from other flexible materials which are nontoxic and impermeable to liquid, for example, an organo siloxane copolymer of the type set forth in U.S. Pat. No. 3,665,520 to Perras, et. al., flexible impermeable polyethylene, polyurethane, Hygron TM and the like. Similarly, the contents may be of any suitable gel or liquid material, the principal requirement being that liquid or gel is nontoxic.

EXAMPLE 1

Figure 1:
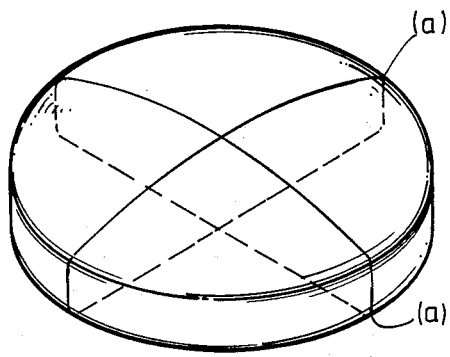
FIG. 1 is an elevational view of a spheroid prosthesis resting on a horizontal flat surface wherein the prosthesis is constructed of silicone gel, saline, or silicone gel and saline contained within a silicone elastomer envelope to which two strips of radioopaque material have been affixed in a pattern or configuration so that one strip encircles the prosthesis in the direction if its X axis and the other strip encircles the prosthesis in the direction of its Y axis.

In this example, reference is made to FIG. 1 which illustrates one presently preferred pattern or configuration for applying the radioopaque label strips (a) to the external surface of the silicone elastomer envelope of a spheroid prosthesis. In this example, the prosthesis is resting on a horizontal flat surface and one label strip has been applied so that it encircles the prosthesis in the direction of its X axis, and the other label strip is applied so that it encircles the prosthesis in the direction of its Y axis. Label strips thus applied intersect on the top and bottom surfaces of the prosthesis when viewed from above.

FIG. 2 shows a mammogram of a prosthesis marked with the configuration or pattern as above which has been implanted in a breast. This figure illustrates the labeled silicone elastomer envelope (a) in complete contact with the surrounding breast tissue (b) establishing that the envelope remains intact.

In contrast, FIG. 3 shows a mammogram of a breast bearing the labeled prosthesis of FIG. 1 in which the prosthetic envelope (a) has ruptured and a small portion of the silicone gel (c) has escaped the envelope. Rupture of the silicone elastomer envelope is established by the change in configuration or pattern of the radioopaque markers.

FIG. 4 shows a mammogram of a breast bearing a labeled prosthesis of FIG. 1 in which the change in the pattern or configuration of the radioopaque marker indicates that the prosthetic envelope (a) has ruptured, and most of the silicone gel (c) has moved out of the envelope. In this figure, so large a quantity of free silicone gel (c) has become interposed between the breast tissue (b) and the silicone elastomer envelope (a) that the labeled envelope (a) has been pushed back against the chest wall (d).

Therefore, because labeled silicone elastomer envelopes of breast prostheses characteristically are forced away from the surrounding tissues by contents escaped to the outside of the envelope, mammography of breasts bearing prostheses labeled as described above provides a reliable method for determining whether the prosthetic silicone elastomer envelope has ruptured.

Application of radioopaque label strips as described in this example also makes possible predicting whether fold-fault failure of the silicone elastomer envelope of implanted prostheses is impending. The mammogram shown in FIG. 2 shows two locations of folding (c) and (d) of the prosthetic envelope. Folding in these same locations of the prosthetic envelope appearing on subsequent mammograms indicates that the folds are persistent and suggests that rupture of the envelope along the fold may occur. Another technique for determining whether a fold is persistent is to compare a mammogram of the breast taken without compressing the breast to the mammogram shown in FIG. 2 which was taken with breast compression along the lateral and medial aspects of the breast. The appearance of a fold in the same location of a mammogram obtained with breast compression and one obtained without breast compression also indicates persistence of the fold. Once a persistent fold in the prosthetic envelope has been detected, procedures to alleviate the fold can be initiated to prevent rupture of the envelope, thus preventing the possibility of having to replace the prosthesis on an emergency basis.

EXAMPLE 2

Figure 8:
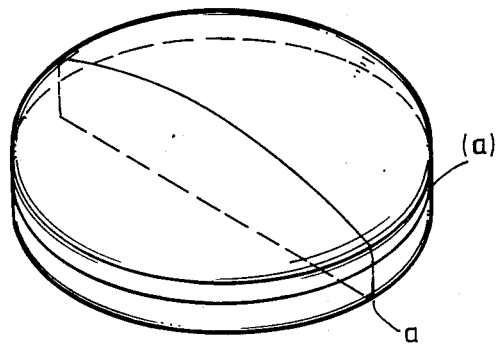
FIG. 8 is an elevational view of a spheroid prosthesis resting on a horizontal flat surface wherein the prosthesis is constructed of silicone gel, saline, or silicone gel and saline contained within a silicone elastomer envelope to which two strips of radioopaque material have been attached in a pattern or configuration so that one strip encircles the prosthesis in its vertical plane and the other strip encircles the prosthesis in its horizontal plane.

In this embodiment of the present invention the same type of breast prosthesis, the same type of radioopaque labeling material, and the same method for attaching the radioopaque material to the silicone elastomer envelope of the prosthesis, as were used in Example 1, were employed. However, in this example, the radioopaque strips were attached in another presently preferred pattern or configuration which differs from that described previously. As shown in FIG. 8, two strips of radioopaque material have been attached to the silicone elastomer envelope so that one strip encircles the prosthesis in its vertical plane, and the other strip encircles the prosthesis in its horizontal plane.

Mammography of breasts bearing prostheses labeled in a pattern or configuration as described in this example also was used to evaluate the status of the prosthesis. As long as the silicone elastomer envelope of the prosthesis remained intact, there was no change in the pattern or configuration of the radioopaque marker. However, once the envelope had ruptured, the labeled silicone elastomer envelope was forced away from the surrounding breast tissue by contents of the envelope resulting in a change in the marker pattern or configuration. Application of radioopaque label strips as described in this example also makes possible use of the method described in Example 1 to predict whether fold-fault failure of the silicone elastomer envelope of implanted prostheses is impending.

EXAMPLE 3

Figure 6:
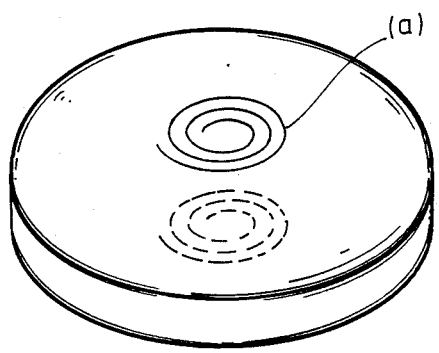
FIG. 6 is an elevational view of a spheroid prosthesis resting on a horizontal flat surface wherein the prosthesis is constructed of silicone gel, saline, or silicone gel and saline contained within a silicone elastomer envelope to which two strips of radioopaque material have been affixed in a pattern or configuration so that one strip is in a coiled configuration on the top surface of the silicone elastomer envelope, and the second strip is in a coiled configuration on the bottom surface of the silicone elastomer envelope.

In this embodiment of the present invention, the same type of breast prosthesis, the same type of radioopaque labeling material, and the same method for attaching the radioopaque material to the silicone elastomer envelope of the prosthesis, as were used in Example 1, were employed. However, in this example, the radioopaque strips were attached in another presently preferred pattern or configuration which differs from that described in the previous example. As shown in FIG. 6, viewing the spheroid prosthesis from above, one strip of radioopaque material (a) was affixed to the top external surface of the silicone elastomer envelope in a coiled configuration; and a second such strip was affixed to the bottom eternal surface of the silicone elastomer envelope in a coiled configuration.

Mammography of breasts bearing prostheses labeled as described in this example also was used to evaluate the status of the prosthesis. As long as the silicone elastomer envelope of a prosthesis remained intact, the pattern or configuration of the strips of opaque material was unchanged. However, once the envelope had ruptured, the configuration or pattern of the labeled silicone elastomer envelope was changed indicating that a portion or potions of the silicone envelope was forced away from the surrounding breast tissue, and silicone gel had migrated from the confines of the envelope was interposed between the breast tissue and the envelope.

EXAMPLE 4

Figure 5:
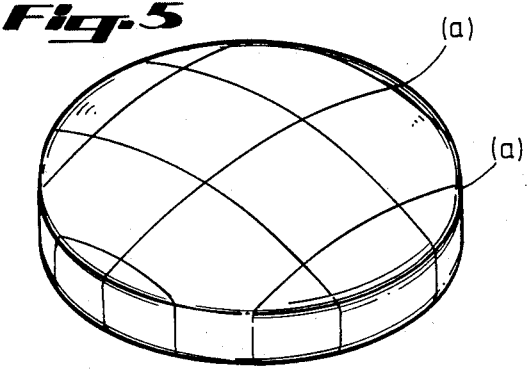
FIG. 5 is an elevational view of a spheroid prosthesis resting on a horizontal flat surface wherein the prosthesis is constructed of silicone gel, saline, or silicone gel and saline contained within a silicone elastomer envelope to which strips of radioopaque material have been affixed in a pattern or configuration so that the strips intersect to form a mesh-like pattern over the entire envelope.

In this embodiment of the present invention, the same type of breast prosthesis, the same type of radioopaque labeling material, and the same method for attaching the radioopaque material to the silicone elastomer envelope of the prosthesis, as were used in Example 1, were employed. However, in this example, the radioopaque strips were attached in a presently preferred pattern or configuration which differs from those described in the previous examples. As shown in FIG. 5, several strips of radioopaque material (a) were affixed to the external surface of the silicone elastomer envelope in a mesh-like configuration encasing the entire envelope. The size of the openings in the mesh shown in FIG. 5 is merely one aspect of the invention; mesh openings much smaller than or larger than those shown in FIG. 5 would perform equally well.

Mammography of breasts bearing the prosthesis labeled in a pattern or configuration as described in this example also was used to evaluate the status of the prosthesis. As long as the silicone elastomer envelope of the prosthesis remained intact, the pattern or configuration remained the same indicating that no silicone gel had escaped from the envelope and migrated between the breast tissue and the labeled prosthetic envelope. However, once the envelope had ruptured, the pattern or configuration of the labeled silicone elastomer envelope was changed indicating that the silicone gel had escaped from the silicone envelope and was interposed between the breast tissue and the envelope. Application of radioopaque label strips in the pattern or configuration as described in this example also make possible use of the method described in Example 1 to predict whether fold-fault failure of the silicone elastomer envelop of implanted prostheses is impending.

EXAMPLE 5

Figure 7:
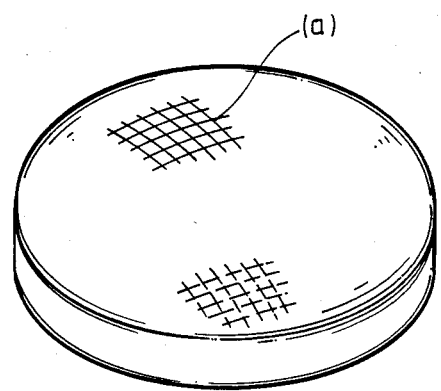
FIG. 7 is an elevational view of a spheroid prosthesis resting on a horizontal flat surface wherein the prosthesis is constructed of silicone gel, saline, or silicone gel and saline contained with a silicone elastomer envelope to which the pattern or configuration is composed of patches of strips of radioopaque material in a mesh-like configuration affixed to the envelope.

In this embodiment of the present invention, the same type of breast prosthesis, the same type of radioopaque labeling material, and the same method for attaching the radioopaque material to the silicone elastomer envelope of the prosthesis, as were used in Example 1, were employed. However, in this example, the radioopaque strips were attached in another presently preferred pattern or configuration which differs from those previously described. As shown in FIG. 7, patches of strips of radioopaque material in a mesh-like configuration (a) were applied to the external surface of the silicone elastomer envelope. As in the previous examples, mammography of breasts bearing prostheses as described in this example was used to determine whether the silicone elastomer envelope of an implanted prosthesis remained intact, had ruptured, or had a fold-fault.

EXAMPLE 6

In this embodiment of the present invention, the same type of breast prosthesis as was used in Example 1 was employed. However, in this example, the entire surface of the silicone elastomer envelope of the prosthesis was labeled with a radioopaque material. Barium sulfate was selected as the radioopaque material. A quantity of barium sulfate sufficient to produce the desired radioopacity was mixed with silicone rubber which was then applied in a thin layer to the silicone elastomer envelope of a prosthesis. The prosthesis was then recured by heating to affix the silicone rubber bearing the radioopaque label to the envelope permanently. Breasts bearing prostheses labeled as described in this example were evaluated by mammography to ascertain whether the prosthetic envelope remained intact. A mammogram with or without a slight pressure showed whether the silicone envelope was intact or had ruptured. No change in the perimeter of the silicone enveloped indicating that there was no rupture; a change in its perimeter indicating that the silicone envelope had ruptured.

The marker can be applied to external surface of the envelope in any desired configuration or pattern, including covering the entire surface of the envelope, or providing a single line marker provided that the marker absorbs electromagnetic energy different than the envelope, its contents, and the human tissue into which it is implanted and is capable of indicating a rupture or a fold-fault of the envelope.

As previously mentioned, the contents of the envelope may be any desired fluid or gel-like material which is nontoxic and can be used in breast prostheses provided it absorbs electromagnetic energy different from the marker and the soft breast tissue; and the envelope may be formed of any impermeable, nontoxic flexible material.

The present invention, therefore, is well suited and adapted to attain the objects and ends and has the advantages and features mentioned as well as other inherent therein.

What is claimed is:

1. A method of determining whether a breast prosthesis implanted in a human breast cavity surrounded by human soft tissue remains intact, has ruptured, or has a fold-fault comprising, implanting into the breast cavity a breast prosthesis comprised of a closed impermeable flexible envelope containing a material selected from the group consisting of liquids, gels, and combinations thereof, to provide and maintain a human breast shape when implanted, the envelope having a radioopaque label on its surface absorbing electromagnetic energy to an extent different from the human soft tissue, the envelope and its contents, the label being in a configuration to indicate a change or no change in the envelope's shape so that, when the breast prosthesis is implanted, no change in the label's configuration indicates that the envelope's shape has not changed and therefore the envelope is intact, and a change in the label's configuration indicates that the shape of the envelope has changed by rupturing or fold-faulting so that, upon obtaining an X-ray image by electromagnetic imaging of the implanted breast prosthesis showing the configuration of the radioopaque label, the envelope is indicated as intact, has ruptured, or has a fold-fault.

2. The method of claim 1 where, the material contained in the envelope is selected from the group consisting of silicone gel, saline and a combination thereof; and the flexible envelope is silicone elastomer.

3. A method of determining whether a breast prosthesis implanted in a human breast cavity surrounded by human soft tissue remains intact, has ruptured, or has a fold-fault comprising, implanting into the breast cavity a breast prosthesis comprised of a closed impermeable flexible envelope containing a material selected from the group consisting of a liquids, gels and combinations thereof to provide and maintain a human breast shape when implanted, the envelope having a radioopaque label on its surface absorbing electromagnetic energy to an extent different from the human soft tissue, the envelope and its contents, no change in the configuration of the radioopaque label indicating that the envelope's shape has not changed and therefore remains intact, a change in the configuration of the label indicating a change in the envelope's shape by rupturing or fold-faulting, and, producing an X-ray image of the implanted breast prosthesis by electromagnetically imaging it which shows the configuration of the radioopaque label thereby indicating that the envelope is intact, has ruptured, or has a fold-fault.

4. The method of claim 3 where,
the material contained in the envelope is selected from the group consisting of silicone gel, saline and a combination thereof; and
the envelope is silicone elastomer.

5. A method of using mammography to determine whether a breast prosthesis implanted in a human breast cavity surrounded by human soft tissue remains intact, has ruptured, or has a fold-fault comprising, implanting into the breast cavity a breast prosthesis comprised of a closed impermeable flexible envelope containing a material selected from the group consisting of liquids, gels and combinations thereof to provide and maintain a human breast shape when implanted, the envelope having a radioopaque label on its surface absorbing electromagnetic energy to an extent different form the human soft tissue, the envelope and the material, the label being in a configuration so that, when the breast prosthesis is implanted, no change in the label's configuration indicates the envelope's shape has not changed and, therefore is intact, and a change in the label's configuration indicates that the silicone elastomer envelope's shape has changed and therefore has ruptured or has a fold-fault, and producing an X-ray image of the implanted breast prosthesis showing the configuration of the radioopaque label thereby indicating that the envelope is intact, has ruptured or has a fold-fault.

6. The method of claim 3 where,
the method is by obtaining a mammogram of a breast having the implanted breast prosthesis when the breast is compressed along its lateral and medial aspects.

7. A method for determining whether a breast prosthesis implanted in human soft tissue comprised of an inner material selected from the group consisting of liquid, gel and combinations thereof and an outer material remains intact, has ruptured, or has a fold-fault comprising, labeling the outer material of the prosthesis with strips of radioopaque material which absorbs electromagnetic energy to an extent different from the human soft tissue, the envelope and its inner material, so that the strips intersect to form a mesh-like pattern over the entire surface of the outer material effective to indicate no change or a change in shape of the envelope, no change in the pattern indicating that the shape of the outer material remains intact, and a change in the pattern indicating that the outer material has ruptured or has a fold-fault, producing an X-ray image of the implanted prosthesis showing the mesh-like pattern by irradiating the human soft tissue into which the prosthesis is implanted, and examining the image to determine if there has been any change in the mesh-like pattern of the radioopaque material.

8. A method for using roentgenography to predict whether fold-fault failure of an implanted closed silicone elastomer envelope breast prosthesis containing silicone gel, saline, or silicone gel and saline is likely to occur, comprising, labeling the prosthetic silicone elastomer envelope with strips of radioopaque material which absorb electromagnetic energy to an extent different from the human soft tissue, the silicone envelope and its contents, and intersect to form a mesh-like pattern over the entire envelope prior to implantation of the prosthesis, no change in the mesh-like pattern indicating that the implanted silicone envelope's shape has not changed and therefore is intact, and a change in the mesh-like pattern indicating that the silicone envelope's shape has changed by rupturing or fold-faulting, obtaining two or more serial roentgenograms of the prosthesis showing the mesh-like pattern after implantation, and comparing the mesh-like pattern of the roentgenograms to determine if there has a persistent fold line in the silicone envelope.

9. A method for using mammography to predict whether fold-fault of an implanted closed silicone elastomer envelope containing silicone gel, saline, or silicone gel and saline is likely to occur, has occurred, or the silicone elastomer envelope has ruptured comprising, labeling the prosthetic silicon elastomer envelope with strips of radioopaque material which absorb electromagnetic energy different from the soft tissue, the envelope and its contents, and intersect to form a mesh-like pattern over the entire envelope prior to implantation of the prosthesis effective to indicate no change or a change in shape of the envelope, no change in the mesh-like pattern indicating that the silicone elastomer envelope is intact, and a change in the mesh-like pattern indicating a fold-fault is likely to occur or has occurred, obtaining a mammogram of a breast bearing the prosthesis showing the mesh-like pattern while the breast is compressed along its lateral and medial aspects, obtaining another mammogram of the breast bearing the label prosthesis showing the mesh-like pattern while the breast is not compressed, and comparing the mesh-like pattern of the roentgenograms to determine if there is a persistent fold line, a rupture in the silicone elastomer envelope, or the silicone elastomer envelope is intact.

10. A breast prosthesis comprising,
an impermeable flexible closed envelope shaped to fit into and be implanted in a human breast cavity to form a human breast shape,
a material selected from the group consisting of fluids, gels and combinations thereof contained in and filling the interior of the envelope to provide and maintain the human breast shape when the envelope is implanted, and
a radioopaque label on the silicone elastomer envelope's surface which absorb electromagnetic energy to an extent different from human soft tissue surrounding the envelope when implanted and the envelope and its content, the radioopaque label being in a configuration to indicate a change or no change in the envelope's shape so that on electromagnetic imaging of the implanted breast prosthesis no change in configuration of the radioopaque marker indicates that the breast prosthesis' shape has not changed and therefore the envelope is intact, and a change in the configuration of the radioopaque marker indicates that the shape of the envelope has changed by rupturing or fold-faulting.

11. The prosthesis of claim 10 where, the material is selected from the group consisting of silicone gel, saline, and the combination of silicone gel and saline; and the envelope is silicone elastomer.

12. The prosthesis of claim 10 where, the radioopaque marker is in a configuration comprising two radioopaque strips affixed to the envelope so that the strips encircle front, back, and sides of the envelope, the strips being at an angle to and intersecting one another.

13. The prosthesis of claim 10 where, the radioopaque marker is in a configuration comprising radioopaque first and second strips so that, when the prosthesis is setting on a horizontal surface, the first strip encircles the envelope in its horizontal plane and the second strip encircles the envelope in its vertical plane.

14. The prosthesis of claim 10 where, the radioopaque marker is in a configuration comprising radioopaque first and second strips, the first strip being in a coiled configuration on the envelope's front surface when implanted, and the second strip being in a coiled configuration on the envelope's back surface when implanted.

15. The prosthesis of claim 10 where, the radioopaque marker is in a configuration comprising radioopaque strips which intersect one another to form a mesh-like pattern encasing all of the envelope.

16. The prosthesis of claim 10 where, the radioopaque marker is in a configuration comprising radioopaque strips forming patches of mesh-like configurations on the envelope.

17. The prosthesis of claim 8 where, the radioopaque marker covers the entire surface of the envelope.

18. A method of determining whether a breast prosthesis implanted in a human breast cavity surrounded by human soft tissue remains intact, has ruptured, or has a fold-fault comprising, obtaining an X-ray image by electromagnetic imaging of the implanted breast prosthesis comprised of an impermeable, closed flexible envelope containing a material selected from the group consisting of liquids, gels and combinations thereof, the material maintaining a breast shape of the breast prosthesis, the envelope having a radioopaque marker on its surface absorbing electromagnetic energy to an extent different from the human soft tissue, the envelope and its contents, the label being in a configuration so that no change in its configuration indicates that the envelope's shape has not changed and therefore is intact, and a change in the label's configuration indicates that the envelope's shape has changed by rupturing or fold-faulting.

19. The method of claim 18 where, the material contained in the envelope is selected from the group consisting of silicone gel, saline, and a combination thereof; and the flexible envelope is silicone elastomer.

* * * * *

UNITED STATES PATENT OFFICE
CERTIFICATE OF CORRECTION

Patent No. 4,795,463                Dated January 3, 1989

Inventor(s) Frank J. Gerow

It is certified that error appears in the above-identified patent and that said Letters Patent is hereby corrected as shown below:

Column 3, line 8, delete "envelop,," and insert
  -- envelope, --
Column 5, line 59, delete "Prosthesis" and insert
  -- prosthesis --
Column 8, line 9, after "invention" insert -- , --
Column 8, line 54, delete "eternal" and insert -- external --
Column 8, line 65, delete "potions" and insert -- portions --
Column 12, line 30, after "fold-fault" insert -- failure --
Column 12, line 68, delete "absorb" and insert -- absorbs --
Column 13, line 3, delete "content" and insert -- contents --

Signed and Sealed this

Thirtieth Day of May, 1989

Attest:

DONALD J. QUIGG

Attesting Officer    Commissioner of Patents and Trademarks